United States Patent
Lozano Platonoff et al.

(10) Patent No.: US 11,623,048 B2
(45) Date of Patent: Apr. 11, 2023

(54) DEVICE FOR MONITORING THE STATE OF AN APPLICATOR FOR INJECTING A MEDICAMENT AND A METHOD OF MONITORING THE STATE OF AN APPLICATOR BY MEANS OF SAID DEVICE

(71) Applicant: NEMERA SZCZECIN SPOLKA Z OGRANICZONA ODPOWIEDZIALNOSCIA, Szczecin (PL)

(72) Inventors: Alberto Lozano Platonoff, Szczecin (PL); Daniel Matias, Szczecin (PL)

(73) Assignee: NEMERA SZCZECIN SPOLKA Z OGRANICZONA ODPOWIEDZIALNOSCIA, Szczecin (PL)

( * ) Notice: Subject to any disclaimer, the term of this patent is extended or adjusted under 35 U.S.C. 154(b) by 226 days.

(21) Appl. No.: 16/976,269

(22) PCT Filed: Mar. 1, 2019

(86) PCT No.: PCT/IB2019/051645
§ 371 (c)(1),
(2) Date: Aug. 27, 2020

(87) PCT Pub. No.: WO2019/167003
PCT Pub. Date: Sep. 6, 2019

(65) Prior Publication Data
US 2020/0405967 A1   Dec. 31, 2020

(30) Foreign Application Priority Data
Mar. 1, 2018   (PL) .......................................... 424735

(51) Int. Cl.
*A61M 5/315* (2006.01)
*A61M 5/31* (2006.01)

(52) U.S. Cl.
CPC .... *A61M 5/31548* (2013.01); *A61M 5/31566* (2013.01); *A61M 2005/3125* (2013.01);
(Continued)

(58) Field of Classification Search
CPC ............ A61M 5/31566; A61M 5/3157; A61M 2205/502; A61M 2005/3125;
(Continued)

(56) References Cited

U.S. PATENT DOCUMENTS

2008/0172027 A1   7/2008   Blomquist
2018/0333330 A1*  11/2018  Nagar ..................... A61M 5/24

FOREIGN PATENT DOCUMENTS

CA   2991686 A1   1/2017
EP   2384778 A1   11/2011
(Continued)

*Primary Examiner* — Deanna K Hall
(74) *Attorney, Agent, or Firm* — Browdy and Neimark, PLLC

(57) ABSTRACT

A device (1) for monitoring the state of an injection applicator comprising an energy source (10) and the following electronic components: an accelerometer (5), a time measuring means (6), a temperature measuring means (7), a processing unit (8) connected to a system adapted to store, process and transfer data, said system including: the time measuring means (6), the accelerometer (5), the temperature measuring means (7) and a memory (9), a user interface (4) connected to the processing unit (8) for presenting information based on the data transferred by the processing unit (8), said monitoring device (1) being connected to a control member (3) of the applicator, and wherein said monitoring device (1) is adapted to operate in a sleep mode and in an active mode, and is further adapted to detect by means of the accelerometer (5) at least a first action and a second action, the first action being related to taking said monitoring device (1) out of the sleep mode and putting it into the active mode, (Continued)

and the second action being related to the setting and/or the delivering of a dose.

16 Claims, 3 Drawing Sheets

(52) U.S. Cl.
  CPC ............... *A61M 2205/3368* (2013.01); *A61M 2205/502* (2013.01); *A61M 2205/52* (2013.01); *A61M 2205/8206* (2013.01)

(58) Field of Classification Search
  CPC ...... A61M 2205/3368; A61M 2205/52; A61M 5/31548
  See application file for complete search history.

(56) References Cited

FOREIGN PATENT DOCUMENTS

| WO | 2015136513 A1 | 9/2015 |
| WO | 2017090019 A2 | 6/2017 |
| WO | 2018028886 A1 | 2/2018 |

* cited by examiner

DEVICE FOR MONITORING THE STATE OF AN APPLICATOR FOR INJECTING A MEDICAMENT AND A METHOD OF MONITORING THE STATE OF AN APPLICATOR BY MEANS OF SAID DEVICE

The present invention concerns a device for monitoring the state of an applicator for injecting a medicament and a method of monitoring the state of an applicator by means of said device.

Medical injectors comprising cartridges with a medicament that are used for regular multiple administration of doses, for example insulin doses, require storage in specific conditions. Moreover, the injections may be carried out according to a specific time schedule which further requires regular monitoring of the actions related to the medicament administration, i.e. both the already performed actions and those planned to be performed in future.

Many solutions are known, enabling the monitoring of the use of medical injectors. For example, injectors equipped with a microprocessor cooperating with temperature sensors, timers and various sensors allowing detection of the events of setting/injecting a dose, as well as recording the amount of the delivered dose, are broadly known. All these elements are usually disposed inside the injector and/or its cap or, alternatively, they constitute an additional equipment in the form of a detachable add-on module, Producers of the described devices strive to develop a compact and simple design that would not be unduly complicated in manufacture and in use.

The aim of the invention is to provide a device for monitoring the state of an applicator for injecting a medicament and a method of monitoring the state of an applicator by means of this device.

A particular aim of the invention is to provide a device and method enabling to measure the storage temperature of the medicament and the time elapsed since the last use of the applicator, as well as to warn the user that the allowed temperature could have been exceeded since the last use of the applicator.

Another aim of the invention is to provide a device which is as compact as possible and whose design would not interfere with the basing control assemblies of the applicator.

According to the invention, a device for monitoring the state of an injection applicator comprising a medicament reservoir and a control member for setting and/or delivering a dose of the medicament by means of a mechanical system, wherein said monitoring device comprises an energy source and the following electronic components:
- an accelerometer;
- a time measuring means;
- a temperature measuring means;
- a processing unit connected to a system adapted to store, process and transfer data, said system including: the time measuring means, the accelerometer, the temperature measuring means and a memory;
- a user interface connected to the processing unit for presenting information based on the data transferred by the processing unit,
- said monitoring device being connected to the control member of the applicator, and
- wherein said monitoring device is adapted to operate in a sleep mode and in an active mode, and is further adapted to detect by means of the accelerometer at least a first action and a second action, the first action being related to taking said monitoring device out of the sleep mode and
- putting it into the active mode, and the second action being related to the setting and/or the delivering of a dose, and
- wherein the data transferred by the processing unit concerns the time stamps assigned to the detected actions and temperature measurements.

Preferably, the processing unit is a device selected from the group including a central processing unit (CPU), a microprocessor, a microcomputer and a logic gates system adapted to assign time stamps to the detected actions.

The processing unit is preferably adapted to process the received data in such a way that the user interface (4) presents the information about the time stamp assigned to the last second action and about the minimal and the maximal temperature measured during the time elapsed since said last second action.

The processing unit may be a microcontroller connected to the time measuring means and the memory.

The device preferably comprises an element connecting the electronic components having a form of a printed circuit board with conductive PCB structures, the printed circuit board being preferably made of an elastic material.

The device is preferably adapted to activate the user interface upon being put into the active mode after the detection of the first action and to deactivate the user interface and being put into the sleep mode after a specified time lapse since the detection of the second action or after a specified period of time of the operation in the sleep mode.

The may be adapted to detect the first action and the second action occurring within a defined time interval after the first action, the first action consisting in a double induction of vibrations of the monitoring device within a time interval of about several hundred milliseconds, the second action consisting in any change of the accelerometer position combined with an induction of vibrations resulting from the operation of said mechanical system.

The device may further be adapted to detect a third action consisting in a double induction of vibrations of the monitoring device within a time interval about several hundred milliseconds, the third action following the second action within a defined time interval.

Preferably, the user interface is further adapted to present information about a low battery status and/or an occurrence of error.

The time measuring means is preferably an RTC module clocked by an external crystal oscillator having a frequency of 32768 Hz.

The user interface is preferably a display.

The display may be selected from the group including: a liquid-crystal display (LCD), a LED display, an OLED display or a display utilizing electronic paper technology.

The processing unit may communicate with the accelerometer, the time measuring means and the temperature measuring means by means of an I²C interface.

According to the invention a method of monitoring the state of an injection applicator is provided, the applicator comprising a medicament reservoir and a control member for setting and/or delivering a dose of the medicament by means of a mechanical system,
the method including the use of a monitoring device comprising an energy source and the following electronic components:

an accelerometer;
a time measuring means;
a temperature measuring means;
a processing unit connected to a system adapted to store, process and transfer data, said system including: the time measuring means, the accelerometer, the temperature measuring means and a memory;
a user interface connected to the processing unit, for presenting information based on the data transferred by the processing unit, said monitoring device being connected to the control member of the applicator and being adapted to operate in a sleep mode and in an active mode, the method further including
performing at least a first action and a second action, the first action being related to taking said monitoring device out of the sleep mode and putting it into the active mode, and the second action being related to the setting and/or the delivering of a dose, said first and second actions being detected by means of the accelerometer, and
obtaining by means of the user interface the data transferred by the processing unit, concerning the time stamps assigned to the detected actions and temperature measurements.

Preferably, the first action consists in double tapping on the monitoring device which results in a double induction of vibrations of said monitoring device within a time interval of about several hundred milliseconds, and in that the second action consists in setting and/or delivering a dose by means of the control member, which is related to operation of said mechanical system, within a defined time interval since the first action.

The method preferably includes a third action performed within a defined time interval since the second action, the third action consisting in a double tapping on the monitoring device which results in a double induction of vibrations of said monitoring device.

Embodiments of the invention are presented in the drawings, wherein.

Figure 1:
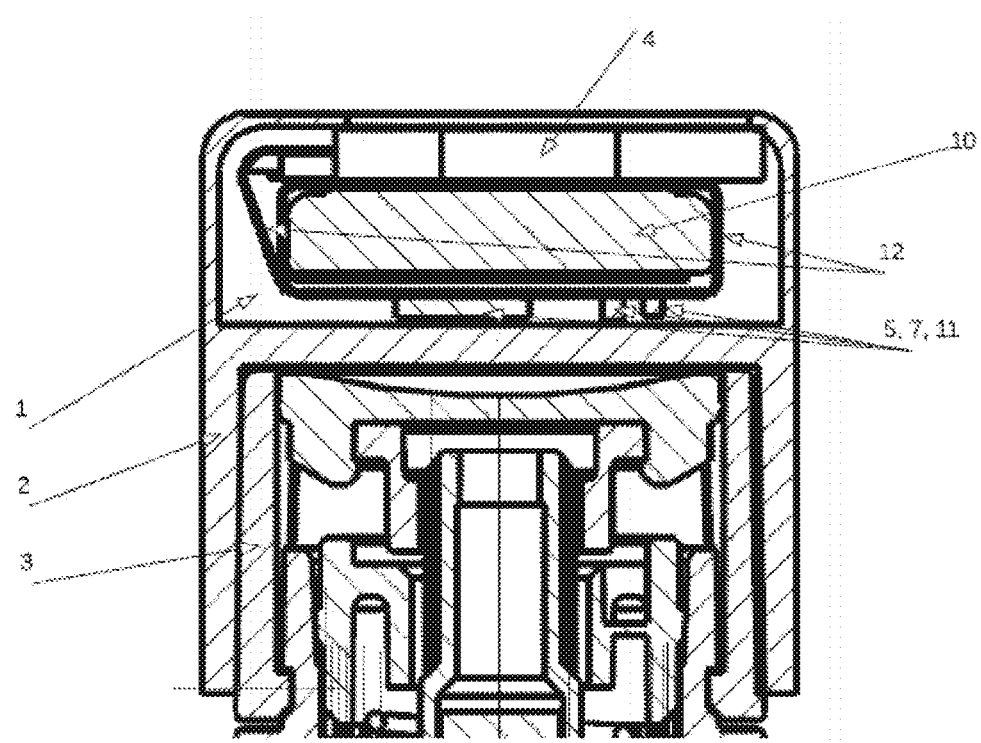
FIG. 1 shows a longitudinal section of the proximal end of an applicator equipped with a device according to the invention.

FIG. 1 shows a device 1 disposed in a cap 2 applied on a control member 3 of an applicator. In this embodiment the control member 3 is a knob for setting a dose but it may also be a button located at the proximal end of the applicator. The cap 2 may be engaged with the knob 3 for example by a push-fit connection. The whole device 1 according to the invention is fitted within a chamber in the cap 2. A user interface 4 constitutes an external wall of the cap 2, which is perpendicular to the axis of the applicator. In this embodiment the user interface is implemented as a display 4 being a part of the device 1 according to the invention. The display 4 may be manufactured e.g. in the liquid crystal technology (LCD), the light emitting diodes (LED) technology, the organic light emitting diodes (OLED) technology or as an electronic quasi-paper display (electronic paper display). The device 1 uses an energy source 10 supplying power to the electronic components.

The device comprises an accelerometer 5, i.e. a device for detecting acceleration changes of the device 1 in which it is located, the changes being recorded in three or more axes of the Cartesian coordinate system. The accelerometer 5 can be a MEMS (microelectromechanical system) accelerometer known in the state of the art.

The device further comprises a time measuring means 6 that may be realized as an internal RTC module, clocked by e.g. an external crystal oscillator having a frequency of 32768 Hz, and a temperature measuring means 7 that may be realized as a known semiconductor sensor with a built-in digital temperature values converter, the digital value of the temperature being stored in a dedicated register of an internal processor.

The temperature data is received by a processing unit 8 at any time intervals, preferably at equal time intervals, for example 30 seconds or 1 minute. The data, i.e. the temperature value is sent from the temperature measuring means 7 via a communication interface.

The processing unit 8 is connected to the time measuring means 6, the accelerometer 5, the temperature measuring means 7 and a memory 9; these components constitute a system adapted to store, process and transfer data. The processing unit 8 is programmed to implement the functions of the device described herein.

The user interface having a form of the display 4 is connected to the processing unit 8. The processing unit 8 transmits the data to the display 4, the data enabling presentation of the required information so that it can be read by the user. The information presented on the display 4 concerns generally time stamps and temperature, which is described in more details below.

A printed circuit board (PCB) having conductive structures embedded thereon constitutes an element integrating the above mentioned electronic components (the accelerometer 5, the time measuring means 6, the temperature measuring means 7, the processing unit 8, the memory 9, the display 4). In the described embodiment, the printed circuit board is made of an elastic material in the known Flexible Printed Circuit (FPC) technology which allows the components disposed on different planes to be integrated on a single board.

Figure 3:
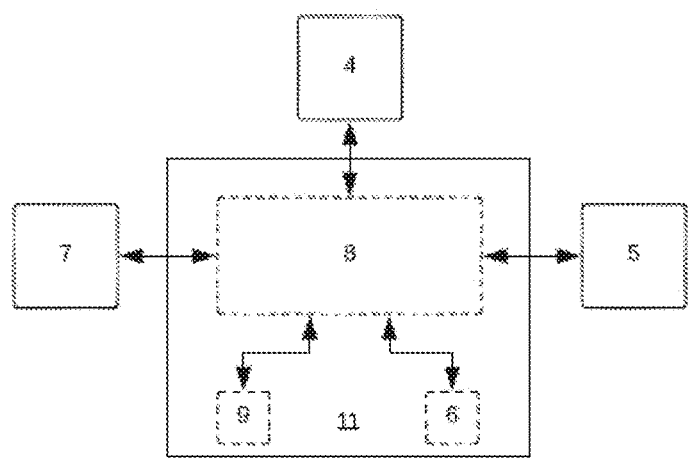
FIG. 3 shows a logical scheme of information exchange between electronic components.

In the preferred embodiment shown in FIG. 1 and FIG. 3, the processing unit 8 is connected to the time measuring means 6 and the memory 9 so as to form a microcontroller 11. If a microcontroller equipped with a system for converting a measured physical value into a numerical value (analog-to-digital converter) is used, another technical implementation enabling temperature measurement is possible. In such case, the processing unit retrieves the data from the temperature measuring means indirectly and converts it to a temperature value.

Figure 4A:
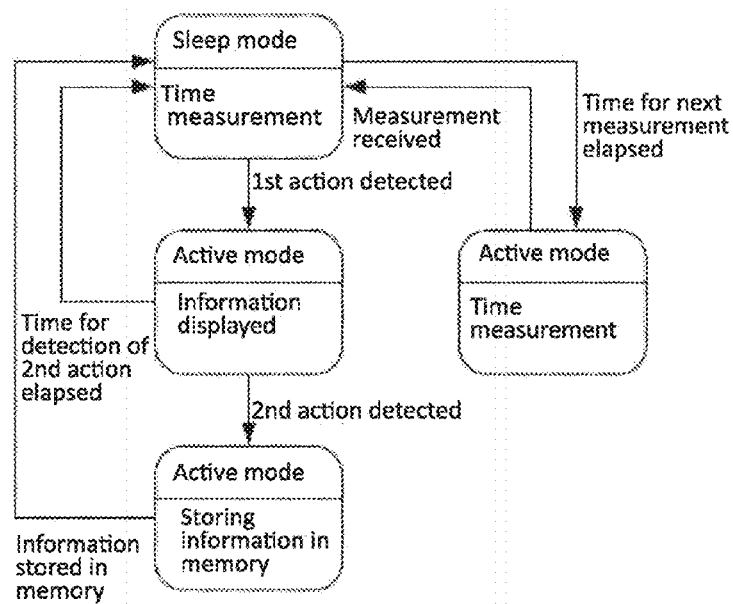
FIGS. 4a and 4b show flowcharts presenting two variants of operation of the device according to the invention, the flowcharts depicting the modes, the performed actions and the events resulting in a change of the mode, related to the essential functions of the device i.e. the detection of an action and the time and temperature measurements.
Figure 4B:
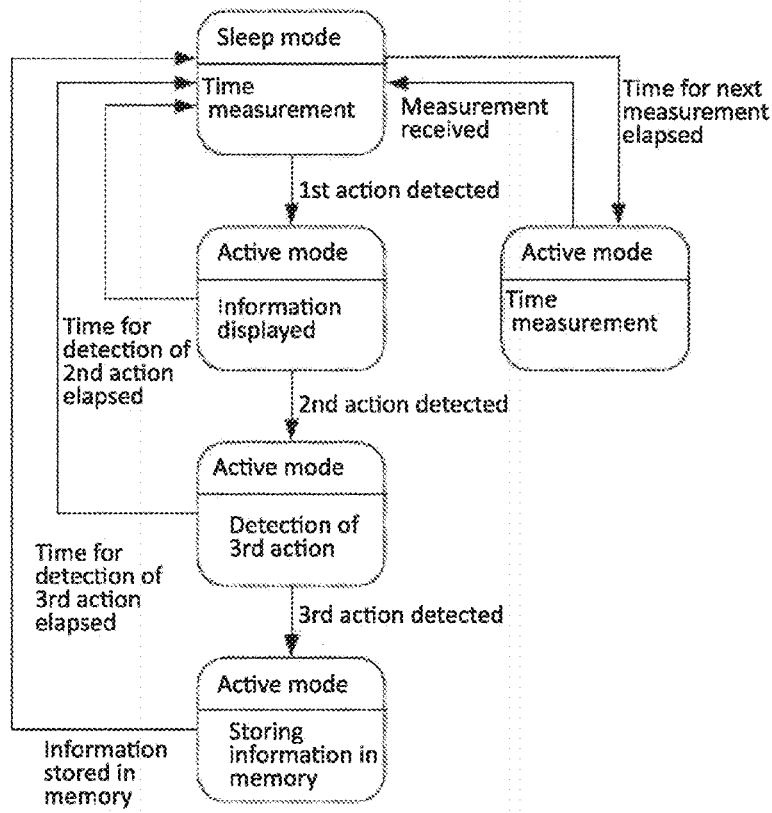

Other embodiments of the device according to the invention are also possible in which the processing unit 8 is a central processing unit (CPU), a microprocessor, a microcomputer or the logic gates system (dedicated or programmable) adapted to carry out the actions described by the flowcharts in FIGS. 4a and 4b.

The energy source 10 may be for example a disposable battery, rechargeable battery or a capacitor connected to a system charging it from an external power source or harvesting energy.

Figure 2:
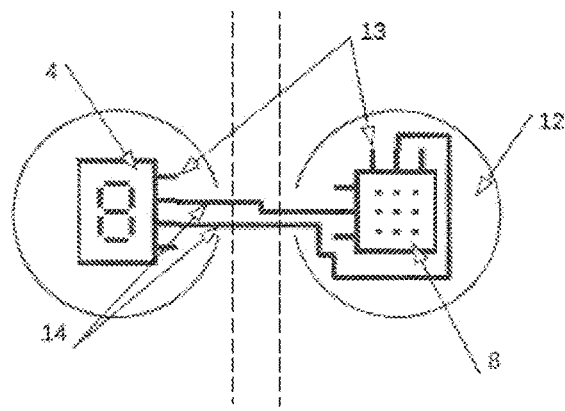
FIG. 2 shows an exemplary arrangement of electronic components on a FPC board.

As can be seen in FIG. 1, the FPC board 12 is disposed in the cap 2 in a way enabling a connection between the display 4, the energy source 10 and the microcontroller 11 as well as the other electronic components (for example the accelerometer 5, the temperature measuring means 7) which are preferably located on the same plane as the microcontroller 11. FIG. 1 shows an exemplary arrangement of the components 5, 7 and 11 as seen in the cross-sections. Their arrangement on a single plane facilitates wiring of the conductive structures 14 shown in FIG. 2. An exemplary arrangement of the electronic components at a part of the FPC board 12 is shown in FIG. 2. In particular, the display 4 and the processing unit 8 are visible. The use of the FPC board is advantageous, as it allows to fold the system by bending it at 90 degrees in the places marked with a dashed line in FIG. 2, in such a way that the display 4 is on the outside.

As can be seen in FIG. 2, the electronic devices and components are equipped with terminals 13 disposed on the outside of the device and enabling a connection with external structures. The PCB board may be made of an elastic material enabling formation of the conductive structures 14 and assembly of the electronic components. In one embodiment it may be a polymeric material with conductive lines printed thereon, the conductive lines connecting the terminals of the electronic components by means of solder joints. The processing unit 8 may be communicated with the accelerometer 5, the time measuring means 6 and the temperature measuring means 7, for example by means of a I$^2$C interface. The I$^2$C interface provides a system of confirmations of data reception, which in turn ensures detection of a presence of the sensor 7 and its proper operation.

In the embodiment shown in FIG. 3, the microcontroller 11 is used (comprising the processing unit 8, the RTC module 6 and the memory 9 connected by an internal bus) and the interface I$^2$C communicates the microcontroller 11 with the temperature measuring means 7 and the accelerometer 5 by means of the SDA and SCL signals (for data and clock, respectively). Inputs/outputs of these signals are located in all the communicated components—the microcontroller 11, the temperature measuring means 7 and the accelerometer 5.

The user interface 4 communicates the following information: the time since the last action of setting of a dose for injection, the highest temperature since the last dose setting, the lowest temperature since the last dose setting and possibly a battery level and the information about detected errors.

The way of operation of the device according to the invention will be described below. A first variant of the operation is depicted by the flowchart in FIG. 4a. The device 1 can be in an active mode or in a sleep mode. Turning the device 1 on (taking it out of the sleep mode and putting it into the active mode) and turning the device 1 off (putting it into the sleep mode) is realized by the suitably programmed processing unit 8. The turning on/off occurs in response to a signal coming from the time measuring means 6, and based on the actions performed by a user and detected by the accelerometer 5.

The time measuring means 6 supplies the processing unit 8 with the information about the elapsing time. When a specified predefined period of time e.g. 60 seconds (other periods may also be set) has elapsed, the processing unit 8 puts the device 1 into the active mode for a temperature measurement to be performed. After the temperature measurement has been completed and the result stored in the memory 9, the processing unit 8 puts the device 1 back into the sleep mode.

The user can perform at least two different actions, the first action being related to taking the device 1 out of the sleep mode and putting it into the active mode, and the second action being related to the setting and/or the delivering of a dose. These actions may be of any kind provided that they are detectable by the accelerometer 5.

The first action may consist for example in a single or multiple tapping on the device 1 (the cap 2), pressing a defined part of the device 1, moving the applicator in a specific manner etc. In the sleep mode a minimal amount of energy, necessary to work properly, is drawn. The sleep mode of the device 1 includes the operation of the time measuring means 6, the accelerometer 5 and the processing unit 8 within the scope required by the sleep mode checking. In the sleep mode of the device 1, the accelerometer 5 works at a lower sampling frequency but the detection of the first action, for example of a double tapping, does not require storing and processing of a large amount of data. The sleep mode substantially reduces energy consumption by the other components for example the temperature measuring means 7.

The second action may consist for example in turning the control member 3 having a form of the knob in order to set or deliver a dose, which involves operation of the mechanical system of the applicator. If the control member has a form of a button, the second action consists in a longitudinal displacement of the button involved with the setting or delivering of the dose.

In the described embodiment, the first action consists in a double tapping on the cap 2 causing a double induction of vibrations of the monitoring device 1 (along with the accelerometer 5) within a time interval of about several hundred milliseconds. The second action is any action which takes place within the defined time interval since the first action, for example within 10 or 20 seconds since the first action, and which causes any change of a position of the device 1. (along with the accelerometer 5), combined with induction of its vibrations caused by the operation of said mechanical system.

The accelerometer 5 transmits a first action detection signal and a second action detection signal to the processing unit 8 and the processing unit 8 activates the respective functions of the device 1 based on these signals.

If the user performs the double tapping within the time interval of about several hundred milliseconds, the accelerometer 5 transmits the first action detection signal to the processing unit 8. Consequently, the processing unit 8 awakes the device 1 (puts it into the active mode) and turns the display 4 on. The display 4 shows the time elapsed since the last detection of an action as well as the highest and the lowest temperatures during this time. If the device 1 is new, the battery has been replaced or, for any reason there is no information about any previous time stamps or recorded temperatures, two horizontal dashes are displayed in a respective location on the display 4. Moreover, in the embodiment with the display 4 embodying the user interface, information about low battery or error occurrence may appear. Two kinds of errors may occur:
 a) a critical error—the device can no longer be used. The critical error occurs when the device detects a condition that would lead to a faulty operation, for example a damage of the temperature measuring means 7 or damage of a the processing unit 8 connection. This is in a situation where the device is still connected to the energy source and able to display information. An "Err" is then displayed, meaning the critical error.

b) a minor error—the device informs the user about it and then is switched to a normal operation mode. The minor error occurs when the device is unable to display the information related to the previously recorded time stamps or temperatures. This may happen for example when the device is new, the battery has been replaced or the battery circuit has been temporarily opened.

In the described embodiment, the second action is detected when the dose is set by turning the knob 3. In order for the device 1 to detect the second action, it must be operating in the active mode after having been awakened by the occurrence of the first action (the active mode is indicated on the operating display 4) and the second action must occur within a defined time interval X, for example 20 seconds, since the detection of the first action. The system, once in the active mode, configures the accelerometer 5 to a higher sampling frequency so that the detection of the second action may be performed with more precision. If the second action is not detected within said time interval X since the first action, the device switches to the sleep mode spontaneously, Said time interval X may be chosen by a person skilled in the art depending on different factors—the mentioned value of 20 seconds is only exemplary. Such way of operation reduces a risk of unintentional reset of a dose counter when a dose has not been delivered. Furthermore, it allows the system to operate with reduced energy demand.

The detection of the second action results in its time stamp being saved in the memory 9 connected to the processing unit 8 and the maximum and minimum temperatures being reset. Then the device 1 starts to measure new maximum and minimum temperatures. Hence, after the detection of the second action, the time measuring means 6, i.e. a timer, continues to measure the time and after a next detection of the first action (awakening of the device) the display 4 will show the time elapsed since the last detection of the second action (the last time stamp saved) and the maximal and minimal temperatures occurred within this time.

If the control member 3 is a knob, the second action is related to its rotational movement during the setting of a dose and the vibrations of the device related to the operation of the mechanical system of the applicator. The function of the accelerometer 5 is to transmit the X, Y, Z change of acceleration data to the processing unit 8, which converts this data in order to identify the rotational movement and the simultaneous vibrations of the mechanical system.

Another possible variant of operation of the device is depicted by the flowchart in FIG. 4b. In this variant also a third intentional action may be detected. The detection of the third action is meant to be a confirmation of the correct detection of the first and second actions. The third action may consist for example (but not necessarily) in a double tapping on the device within a time interval about several hundred milliseconds, the same as the first action. However, this double tapping will be identified as the third action only if it occurs within a defined time interval Y since the detection of the second action. The detection of the third action is a precondition for the time stamp of the second action to be saved in the memory.

This embodiment of the device according to the invention allows to eliminate the risk of a situation where the device is awakened and then a detection of an apparent second action occurs although in fact the dose has not been delivered. This may be the case if the applicator is subject to position changes and vibrations erroneously identified by the device 1 as the second action. In this embodiment, the user can delete the erroneously detected second action.

The invention claimed is:

1. A device for monitoring the state of an injection applicator comprising a medicament reservoir and a control member for setting and/or delivering a dose of the medicament by means of a mechanical system,
   wherein said monitoring device comprises an energy source and the following electronic components:
   an accelerometer;
   a time measuring means;
   a temperature measuring means;
   a processing unit connected to a system adapted to store, process and transfer data, said system including: the time measuring means, the accelerometer, the temperature measuring means and a memory;
   a user interface connected to the processing unit for presenting information based on the data transferred by the processing unit,
   wherein said monitoring device being connected to the control member of the applicator, and
   wherein said monitoring device is configured to operate in a sleep mode and in an active mode, and is further configured to detect by the accelerometer at least a first action and a second action, the first action being related to taking said monitoring device out of the sleep mode and putting it into the active mode, and the second action being related to the setting and/or the delivering of a dose, and
   wherein the data transferred by the processing unit concerns the time stamps assigned to the detected actions and temperature measurements.

2. The monitoring device according to claim 1, wherein the processing unit is a device selected from the group including a central processing unit (CPU), a microprocessor, a microcomputer and a logic gates system adapted to assign time stamps to the detected actions.

3. The monitoring device according to claim 1, wherein the processing unit is configured to process the received data in such a way that the user interface presents the information about the time stamp assigned to the last second action and about the minimal and the maximal temperature measured during the time elapsed since said last second action.

4. The monitoring device according to claim 1, wherein the processing unit is a microcontroller connected to the time measuring means and the memory.

5. The monitoring device according to claim 1, further comprising an element connecting the electronic components having a form of a printed circuit board with conductive PCB structures, the printed circuit board being optionally made of an elastic material.

6. The monitoring device according to claim 1, wherein the processing unit is configured to activate the user interface upon being put into the active mode after the detection of the first action and to deactivate the user interface and being put into the sleep mode after a specified time lapse since the detection of the second action or after a specified period of time of the operation in the sleep mode.

7. The monitoring device according to claim 1, wherein the processing unit is configured to detect the first action and the second action occurring within a defined time interval after the first action,
   the first action consisting in a double induction of vibrations of the monitoring device within a time interval of about several hundred milliseconds,
   the second action consisting in any change of the accelerometer position combined with an induction of vibrations resulting from the operation of said mechanical system.

8. The monitoring device according to claim 7, wherein the processing unit is configured to detect a third action consisting in a double induction of vibrations of the monitoring device within a time interval about several hundred milliseconds, the third action following the second action within a defined time interval.

9. The monitoring device according to claim 1, wherein the user interface is further configured to present information about a low battery status and/or an occurrence of error.

10. The monitoring device according to claim 1, wherein the time measuring means is an RTC module clocked by an external crystal oscillator having a frequency of 32768 Hz.

11. The monitoring device according to claim 1, wherein the user interface is a display.

12. The monitoring device according to claim 11, wherein the display is selected from the group including: a liquid crystal display (LCD), a LED display, an OLED display or a display utilizing electronic paper technology.

13. The monitoring device according to claim 1, wherein the processing unit communicates with the accelerometer, the time measuring means and the temperature measuring means by means of an I²C interface.

14. A method of monitoring the state of an injection applicator comprising a medicament reservoir and a control member for setting and/or delivering a dose of the medicament by a mechanical system, the method including the use of a monitoring device comprising an energy source and the following electronic components:
   an accelerometer;
   a time measuring means;
   a temperature measuring means;
   a processing unit connected to a system adapted to store, process and transfer data, said system including: the time measuring means, the accelerometer, the temperature measuring means and a memory;
   a user interface connected to the processing unit, for presenting information based on the data transferred by the processing unit,
   said monitoring device being connected to the control member of the applicator and being adapted to operate in a sleep mode and in an active mode,
   the method further including
   performing at least a first action and a second action, the first action being related to taking said monitoring device out of the sleep mode and putting it into the active mode, and the second action being related to the setting and/or the delivering of a dose, said first and second actions being detected by means of the accelerometer, and
   obtaining by the user interface (4) the data transferred by the processing unit, concerning the time stamps assigned to the detected actions and temperature measurements.

15. The method according to claim 14, wherein the first action consists in double tapping on the monitoring device which results in a double induction of vibrations of said monitoring device within a time interval of about several hundred milliseconds, and in that the second action consists in setting and/or delivering a dose by the control member, which is related to operation of said mechanical system, within a defined time interval since the first action.

16. The method according to claim 14, further including a third action performed within a defined time interval since the second action, the third action consisting in a double tapping on the monitoring device which results in a double induction of vibrations of said monitoring device.

* * * * *